(12) United States Patent
Park et al.

(10) Patent No.: US 11,467,146 B2
(45) Date of Patent: Oct. 11, 2022

(54) PORTABLE APPARATUS FOR MEASURING AIR QUALITY AND METHOD FOR DISPLAYING INFORMATION ABOUT AIR QUALITY

(71) Applicant: Samsung Electronics Co., Ltd., Gyeonggi-do (KR)

(72) Inventors: Hyuncheol Park, Gyeonggi-do (KR); Changyong Yim, Gyeonggi-do (KR); Ikjoo Byun, Gyeonggi-do (KR); Seongmin Je, Gyeonggi-do (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 328 days.

(21) Appl. No.: 16/840,572

(22) Filed: Apr. 6, 2020

(65) Prior Publication Data

US 2020/0326321 A1 Oct. 15, 2020

(30) Foreign Application Priority Data

Apr. 9, 2019 (KR) .................. KR10-2019-0041125

(51) Int. Cl.
*G01N 9/00* (2006.01)
*G01N 33/00* (2006.01)
(Continued)

(52) U.S. Cl.
CPC ......... *G01N 33/0063* (2013.01); *G01C 21/20* (2013.01); *G01P 13/00* (2013.01); *G01S 19/01* (2013.01)

(58) Field of Classification Search
CPC .. B60H 1/00771; B60H 3/0608; B60H 1/008; B60H 1/00985; B60H 1/00764; B60H 3/0085
(Continued)

(56) References Cited

U.S. PATENT DOCUMENTS 8,092,285 B2 * 1/2012 Mathur .............. B60H 1/00764
454/75
8,145,383 B2 * 3/2012 Prokhorov ............. B60H 1/008
454/75

(Continued)

FOREIGN PATENT DOCUMENTS

CN 101140288 A * 3/2008
CN 201307022 Y 9/2009
(Continued)

OTHER PUBLICATIONS

European Search Report dated Jun. 24, 2020.
International Search Report dated Jul. 27, 2020.
Office Action dated May 27, 2022.

*Primary Examiner* — David Q Nguyen
(74) *Attorney, Agent, or Firm* — Cha & Reiter, LLC

(57) ABSTRACT

Disclosed is an apparatus for measuring air quality, the apparatus comprises a first sensor circuit; a second sensor circuit; a third sensor circuit; a communication circuit configured to communicate with an external server; a display; a processor; and a memory, wherein the memory stores instructions that, when executed, cause the processor to: detect air quality related information by using the first sensor circuit, obtain at least one of movement information detected by using the second sensor circuit or adjacent environment information detected by using the third sensor circuit while the air quality related information is detected, determine validity of the air quality related information from using the first sensor circuit based on the adjacent environment information or the movement information, display the air quality related information from using the first sensor circuit or air quality related information received from the external server based on the determined validity.

20 Claims, 12 Drawing Sheets

(51) Int. Cl.
*G01C 21/20* (2006.01)
*G01P 13/00* (2006.01)
*G01S 19/01* (2010.01)

(58) Field of Classification Search
USPC .................... 700/276; 454/158; 73/31.02
See application file for complete search history.

(56) References Cited

U.S. PATENT DOCUMENTS

| | | |
|---|---|---|
| 10,135,960 B2 | 11/2018 | Han et al. |
| 10,165,406 B2 | 12/2018 | Hong et al. |
| 10,168,190 B2 | 1/2019 | Lee |
| 10,226,982 B2* | 3/2019 | Alger ................ B60H 1/008 |
| 11,023,347 B2 | 6/2021 | Kim et al. |
| 2011/0251800 A1* | 10/2011 | Wilkins ............. G01J 3/0264 |
| | | 702/24 |
| 2013/0080053 A1 | 3/2013 | Rakshit |
| 2013/0278427 A1 | 10/2013 | Setton |
| 2015/0032264 A1* | 1/2015 | Emmons ........... F24F 11/0001 |
| | | 700/276 |
| 2015/0073741 A1 | 3/2015 | Wuest et al. |
| 2015/0292920 A1 | 10/2015 | Lee |
| 2017/0041751 A1 | 2/2017 | Hong et al. |
| 2017/0245782 A1 | 8/2017 | Howard et al. |
| 2017/0274737 A1* | 9/2017 | Delaruelle ......... B60H 1/00771 |
| 2018/0260295 A1 | 9/2018 | Kim et al. |
| 2018/0299419 A1 | 10/2018 | Li |
| 2018/0333101 A1 | 11/2018 | DeBates et al. |
| 2018/0364040 A1 | 12/2018 | Seo et al. |

FOREIGN PATENT DOCUMENTS

| | | |
|---|---|---|
| CN | 105866332 A | 8/2016 |
| CN | 106441326 A | 2/2017 |
| CN | 107238680 A | 10/2017 |
| CN | 108572588 A | 9/2018 |
| CN | 208398898 U | 1/2019 |
| EP | 2846135 A2 | 3/2015 |
| EP | 3240272 A1 | 11/2017 |
| JP | 2005-132246 A | 5/2005 |
| KR | 10-2011-0021215 A | 3/2011 |
| KR | 10-2012-0128199 A | 11/2012 |
| KR | 10-1627788 B1 | 6/2016 |
| KR | 10-2016-0134107 A | 11/2016 |
| KR | 10-1814188 B1 | 1/2018 |
| KR | 10-2018-0094699 A | 8/2018 |
| WO | WO-2016129715 A1 * | 8/2016 |

* cited by examiner

| MEASUREMENT TIME | LOCATION | $SO_2$ | $CO_2$ | $O_3$ | $NO_2$ | PM2.5 | ... | Outdoor /Indoor | VALIDITY |
|---|---|---|---|---|---|---|---|---|---|
| 201808814 10:31:15 | 37.423714 126.993055 | 10 | 550 | 0.01 | 300 | 15 | | Outdoor | 9.8 |
| 201808814 10:33:16 | 37.423546 126.993307 | 5 | 580 | 0.02 | 330 | 18 | | Outdoor | 9.8 |
| 201808814 10:38:20 | 37.423710 126.993480 | 1 | 650 | 0.1 | 350 | 44 | | Indoor | 6.8 |
| 201808814 10:45:25 | 37.423447 126.993502 | 0 | 1000 | 0.02 | 80 | 5 | | Outdoor | 1.3 |
| ... | | | | | | | | | |

FIG. 4

PORTABLE APPARATUS FOR MEASURING AIR QUALITY AND METHOD FOR DISPLAYING INFORMATION ABOUT AIR QUALITY

CROSS-REFERENCE TO RELATED APPLICATION(S)

This application is based on and claims priority under 35 U.S.C. § 119 to Korean Patent Application No. 10-2019-0041125, filed on Apr. 9, 2019, in the Korean Intellectual Property Office, the disclosure of which is incorporated by reference herein its entirety.

BACKGROUND

1. Field

The disclosure relates to a technology of providing air quality information.

2. Description of Related Art

An air quality analysis system may collect air quality related information (e.g., nitrogen dioxide, carbon dioxide, carbon monoxide, fine dust, temperature/humidity, barometric pressure, or the like) from air quality measurement devices having air quality measurement sensor(s). The air quality analysis system can identify the air quality based on the collected information. However, because the air quality measurement devices are not commonly in places such as roofs of buildings, the resolution of the information is not only low, but also different from the air quality of the user's surrounding environment.

The above information is presented as background information only to assist with an understanding of the disclosure. No determination has been made, and no assertion is made, as to whether any of the above might be applicable as prior art with regard to the disclosure.

SUMMARY

In accordance with an aspect of the disclosure, an apparatus for measuring air quality, the apparatus comprises a first sensor circuit configured to sense an external air quality; a second sensor circuit configured to sense a movement of the apparatus; a third sensor circuit configured to sense an environment of the apparatus; a communication circuit configured to communicate with an external server; a display; a processor; and a memory, wherein the memory stores instructions that, when executed, cause the processor to: detect air quality related information by using the first sensor circuit, obtain at least one of movement information detected by using the second sensor circuit or adjacent environment information detected by using the third sensor circuit while the air quality related information is detected by the first sensor circuit, determine validity of the air quality related information from using the first sensor circuit based on at least one of the adjacent environment information or the movement information, display the air quality related information from using the first sensor circuit through the display when the determined validity is equal to or greater than a threshold value, and display air quality related information received from the external server through the display when the determined validity is less than the threshold value.

In accordance with another aspect of the disclosure, a method of displaying air quality related information through an air quality measurement apparatus, the method comprising detecting air quality related information by using a first sensor circuit; obtaining at least one of movement information detected by using a second sensor circuit or adjacent environment information detected by using a third sensor circuit while the air quality related information is detected by the first sensor circuit; determining validity of the air quality related information from the first sensor circuit based on at least one of the adjacent environment information or the movement information; displaying the air quality related information from the first sensor circuit through the display when the determined validity is equal to or greater than a threshold value; and displaying air quality related information received from an external server when the determined validity is less than the threshold value.

Other aspects, advantages, and salient features of the disclosure will become apparent to those skilled in the art from the following detailed description, which, taken in conjunction with the annexed drawings, discloses certain embodiments of the disclosure.

BRIEF DESCRIPTION OF THE DRAWINGS

The above and other aspects, features, and advantages of certain embodiments of the disclosure will be more apparent from the following description taken in conjunction with the accompanying drawings, in which:

FIG. 4 is a view illustrating first air quality related information stored in a memory according to an embodiment;

With regard to description of drawings, similar elements may be marked by similar reference numerals.

DETAILED DESCRIPTION

In order to increase the resolution of the information and to provide the air quality of the user's surrounding environment, the air quality analysis system may uses an air quality measurement sensor arranged around the user. However, it may be difficult to secure a space for installing stationary air quality measurement devices around a user.

Aspects of the disclosure may address at least the above-mentioned problems and/or disadvantages and may provide at least the advantages described below. Accordingly, an aspect of the disclosure may provide a portable apparatus for measuring an air quality, which is capable of providing air quality related information around a user, and a method of displaying the air quality related information.

Figure 1:
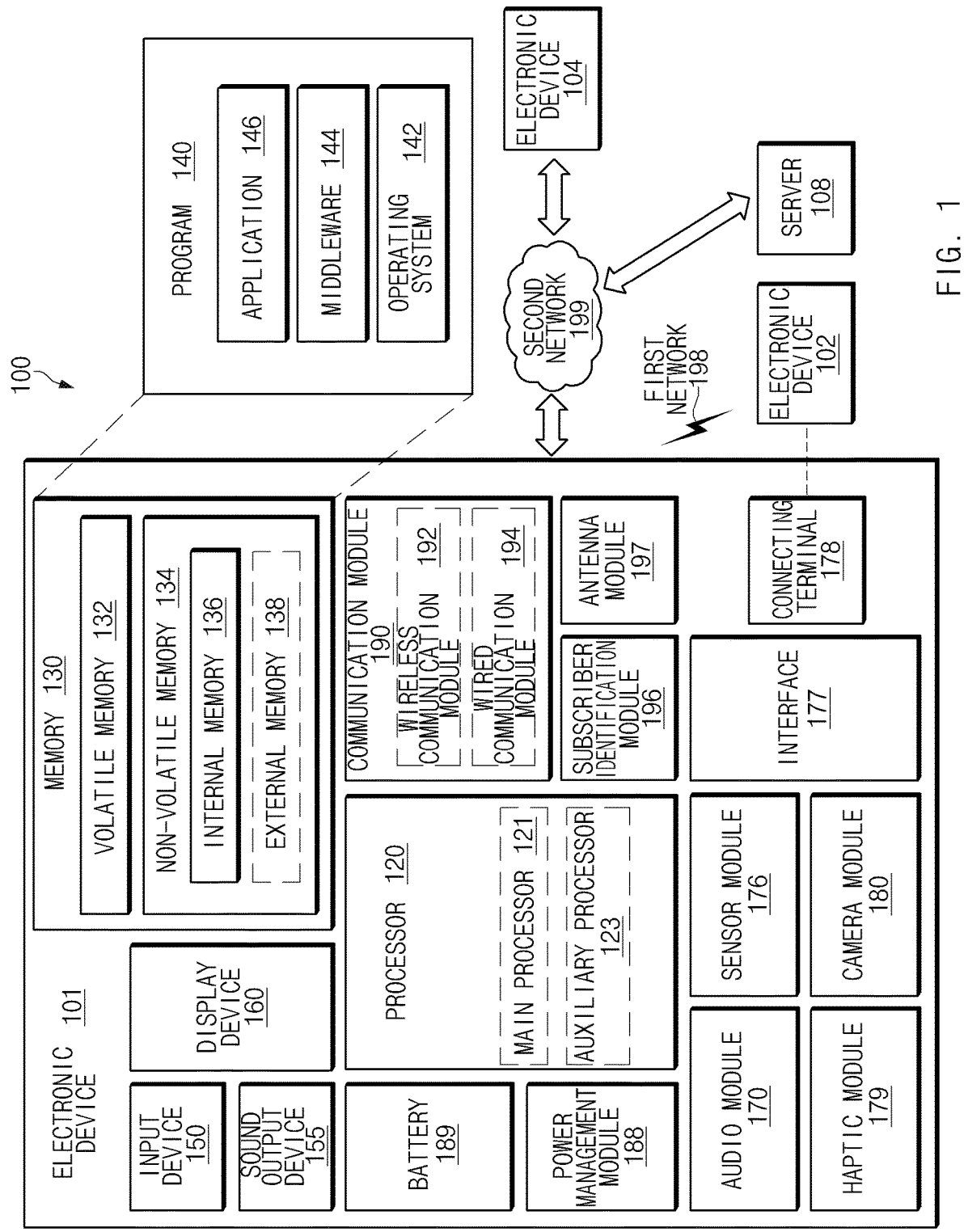
FIG. 1 is a block diagram illustrating an electronic device in a network environment according to certain embodiments.

FIG. 1 is a block diagram illustrating an electronic device 101 in a network environment 100 according to certain embodiments. Referring to FIG. 1, the electronic device 101 in the network environment 100 may communicate with an electronic device 102 via a first network 198 (e.g., a short-range wireless communication network), or an electronic device 104 or a server 108 via a second network 199 (e.g., a long-range wireless communication network). According to an embodiment, the electronic device 101 may communicate with the electronic device 104 via the server 108. According to an embodiment, the electronic device 101 may include a processor 120, memory 130, an input device 150, a sound output device 155, a display device 160, an audio module 170, a sensor module 176, an interface 177, a haptic module 179, a camera module 180, a power management module 188, a battery 189, a communication module 190, a subscriber identification module(SIM) 196, or an antenna module 197. In some embodiments, at least one (e.g., the display device 160 or the camera module 180) of the components may be omitted from the electronic device 101, or one or more other components may be added in the electronic device 101. In some embodiments, some of the components may be implemented as single integrated circuitry. For example, the sensor module 176 (e.g., a fingerprint sensor, an iris sensor, or an illuminance sensor) may be implemented as embedded in the display device 160 (e.g., a display).

The processor 120 may execute, for example, software (e.g., a program 140) to control at least one other component (e.g., a hardware or software component) of the electronic device 101 coupled with the processor 120, and may perform various data processing or computation. According to one embodiment, as at least part of the data processing or computation, the processor 120 may load a command or data received from another component (e.g., the sensor module 176 or the communication module 190) in volatile memory 132, process the command or the data stored in the volatile memory 132, and store resulting data in non-volatile memory 134. According to an embodiment, the processor 120 may include a main processor 121 (e.g., a central processing unit (CPU) or an application processor (AP)), and an auxiliary processor 123 (e.g., a graphics processing unit (GPU), an image signal processor (ISP), a sensor hub processor, or a communication processor (CP)) that is operable independently from, or in conjunction with, the main processor 121. Additionally or alternatively, the auxiliary processor 123 may be adapted to consume less power than the main processor 121, or to be specific to a specified function. The auxiliary processor 123 may be implemented as separate from, or as part of the main processor 121.

The auxiliary processor 123 may control at least some of functions or states related to at least one component (e.g., the display device 160, the sensor module 176, or the communication module 190) among the components of the electronic device 101, instead of the main processor 121 while the main processor 121 is in an inactive (e.g., sleep) state, or together with the main processor 121 while the main processor 121 is in an active state (e.g., executing an application). According to an embodiment, the auxiliary processor 123 (e.g., an image signal processor or a communication processor) may be implemented as part of another component (e.g., the camera module 180 or the communication module 190) functionally related to the auxiliary processor 123.

The memory 130 may store various data used by at least one component (e.g., the processor 120 or the sensor module 176) of the electronic device 101. The various data may include, for example, software (e.g., the program 140) and input data or output data for a command related thereto. The memory 130 may include the volatile memory 132 or the non-volatile memory 134.

The program 140 may be stored in the memory 130 as software, and may include, for example, an operating system (OS) 142, middleware 144, or an application 146.

The input device 150 may receive a command or data to be used by other component (e.g., the processor 120) of the electronic device 101, from the outside (e.g., a user) of the electronic device 101. The input device 150 may include, for example, a microphone, a mouse, a keyboard, or a digital pen (e.g., a stylus pen).

The sound output device 155 may output sound signals to the outside of the electronic device 101. The sound output device 155 may include, for example, a speaker or a receiver. The speaker may be used for general purposes, such as playing multimedia or playing record, and the receiver may be used for an incoming calls. According to an embodiment, the receiver may be implemented as separate from, or as part of the speaker.

The display device 160 may visually provide information to the outside (e.g., a user) of the electronic device 101. The display device 160 may include, for example, a display, a hologram device, or a projector and control circuitry to control a corresponding one of the display, hologram device, and projector. According to an embodiment, the display device 160 may include touch circuitry adapted to detect a touch, or sensor circuitry (e.g., a pressure sensor) adapted to measure the intensity of force incurred by the touch.

The audio module 170 may convert a sound into an electrical signal and vice versa. According to an embodiment, the audio module 170 may obtain the sound via the input device 150, or output the sound via the sound output device 155 or a headphone of an external electronic device (e.g., an electronic device 102) directly (e.g., wiredly) or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly (e.g., wiredly) or wirelessly. According to an embodiment, the interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). According to an embodiment, the connecting terminal 178 may include, for example, a HDMI connector, a USB connector, a SD card connector, or an audio connector (e.g., a headphone connector).

The haptic module 179 may convert an electrical signal into a mechanical stimulus (e.g., a vibration or a movement) or electrical stimulus which may be recognized by a user via his tactile sensation or kinesthetic sensation. According to an embodiment, the haptic module 179 may include, for example, a motor, a piezoelectric element, or an electric stimulator.

The camera module 180 may capture a still image or moving images. According to an embodiment, the camera module 180 may include one or more lenses, image sensors, image signal processors, or flashes.

The power management module 188 may manage power supplied to the electronic device 101. According to one embodiment, the power management module 188 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently from the processor 120 (e.g., the application processor (AP)) and supports a direct (e.g., wired) communication or a wireless communication. According to an embodiment, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device via the first network 198 (e.g., a short-range communication network, such as Bluetooth™ wireless-fidelity (Wi-Fi) direct, or infrared data association (IrDA)) or the second network 199 (e.g., a long-range communication network, such as a cellular network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 192 may identify and authenticate the electronic device 101 in a communication network, such as the first network 198 or the second network 199, using subscriber information (e.g., international mobile subscriber identity (IMSI)) stored in the subscriber identification module 196.

The antenna module 197 may transmit or receive a signal or power to or from the outside (e.g., the external electronic device) of the electronic device 101. According to an embodiment, the antenna module 197 may include an antenna including a radiating element composed of a conductive material or a conductive pattern formed in or on a substrate (e.g., PCB). According to an embodiment, the antenna module 197 may include a plurality of antennas. In such a case, at least one antenna appropriate for a communication scheme used in the communication network, such as the first network 198 or the second network 199, may be selected, for example, by the communication module 190 (e.g., the wireless communication module 192) from the plurality of antennas. The signal or the power may then be transmitted or received between the communication module 190 and the external electronic device via the selected at least one antenna. According to an embodiment, another component (e.g., a radio frequency integrated circuit (RFIC)) other than the radiating element may be additionally formed as part of the antenna module 197.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. Each of the electronic devices 102 and 104 may be a device of a same type as, or a different type, from the electronic device 101. According to an embodiment, all or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, or client-server computing technology may be used, for example.

Figure 2:
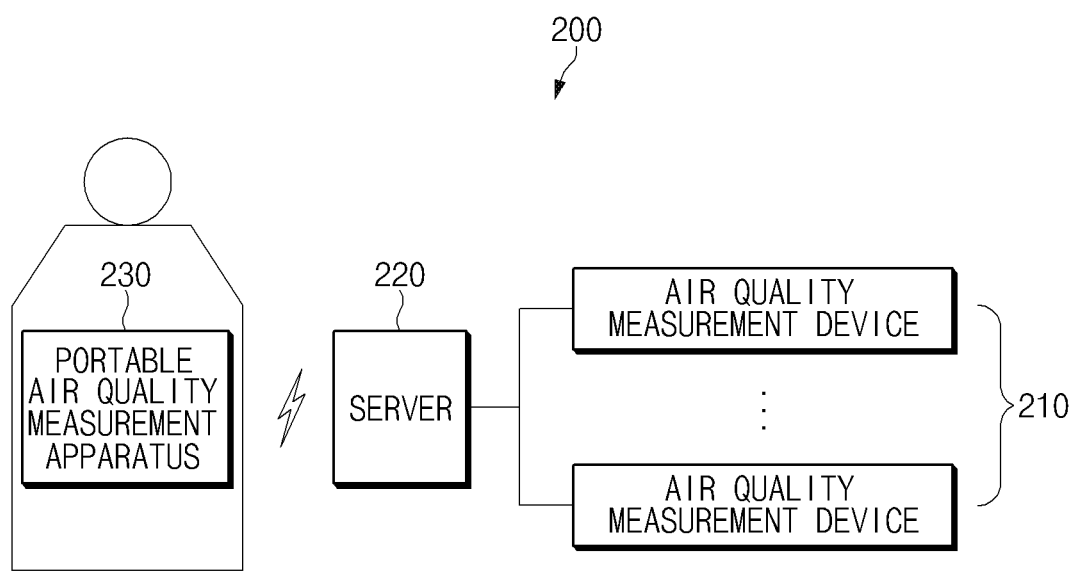
FIG. 2 a block diagram illustrating an air quality measurement system according to an embodiment.

FIG. 2 a block diagram illustrating an air quality measurement system according to an embodiment.

The air quality measurement system may include a portable air quality measurement apparatus 230 that is associated with the user. A network of air quality measurement devices 210 may be deployed in relatively static locations, and interconnected by a server 220. The server 220 maintains air quality information at the locations of the air quality measurement devices 210. The portable air quality measurement apparatus 230 can user air quality information measured by one of the air quality measurement device 210 instead of air quality information measured by itself, in certain circumstances.

For example, the portable air quality measurement apparatus 230 includes a sensor for measuring the air quality, a sensor for measuring movement, and a sensor for measuring the external environment. The portable air quality measurement apparatus 230 may use air quality information from one of air quality measurement devices 210, when the portable air quality measurement apparatus 230 has moved a large distance, or has no valid air quality related information due to the external environment.

Referring to FIG. 2, an air quality measurement system 200 according to an embodiment may include a plurality of air quality measurement devices 210 (e.g., the electronic device 104 of FIG. 1), a server 220 (e.g., the server 108 of FIG. 1), and a portable air quality measurement apparatus 230 (e.g., the electronic device 101 of FIG. 1).

According to an embodiment, the plurality of air quality measurement devices 210 may include an air quality measurement apparatus fixedly installed outdoors or indoors. Each air quality measurement apparatus 210 may include a sensor circuit, determine air quality related information by using the sensor circuit, and transmit the determined air quality related information to the server 220. The air quality related information may include at least one of fine dust (e.g., PM1, PM2.5, PM10, and the like) information or gas ($CO_2$, $NO_2$, $SO_2$, CO, NO, $O_3$, $NH_3$, $H_2S$, total volatile organic compounds (TVOC), volatile organic compounds (VOC), formaldehyde (HCHO), benzene, toluene, ethyl benzene and xylene (BTEX), and the like) information. The fine dust information may include a fine dust index or a grade of fine dust. The gas information may include a gas index or a gas grade. According to certain embodiments, the plurality of air quality measurement devices 210 may include another portable air quality measurement apparatus (not shown).

According to an embodiment, the server 220 may communicate with the plurality of air quality measurement devices 210 and the portable air quality measurement apparatus 230 through a network (e.g., the first or second network 198 or 199 of FIG. 1). The server 220 may store the air quality related information received from the plurality of air quality measurement devices 210 in relation to local information, such as a table of locations of the air quality measurement devices with the measured air quality related information. When the server 220 receives a request for air quality related information from the portable air quality measurement apparatus 230, the server 220 may transmit second air quality related information corresponding to the location of the portable air quality measurement apparatus 230 to the portable air quality measurement apparatus 230.

According to an embodiment, the portable air quality measurement apparatus 230 as a device possessed by a user may include a portable communication device (e.g., a smartphone), a portable computer device, a portable multimedia device, a portable medical device, a portable camera, and a wearable device. The portable air quality measurement apparatus 230 according to an embodiment of the disclosure is not limited to the above-described devices.

According to an embodiment, the portable air quality measurement apparatus 230 may include a first sensor circuit capable of sensing air quality, a second sensor circuit capable of sensing movement, and a third sensor circuit capable of sensing environmental information. The portable air quality measurement apparatus 230 may detect air quality related information by using the first sensor circuit. The portable air quality measurement apparatus 230 can detect movement information (e.g., an acceleration value by a gyroscope, for example) of the portable air quality measurement apparatus 230 by using the second sensor circuit while detecting the air quality related information. The portable air quality measurement apparatus 230 can detect surrounding environment information of the portable air quality measurement apparatus 230 by using the third sensor circuit. In the following description, for convenience of description, the air quality related information detected by the portable air quality measurement apparatus 230 itself is referred to as first air quality related information, and the air quality related information received from the server 220 is referred to as second air quality related information.

The portable air quality measurement apparatus 230 may identify the validity of the first air quality related information. The confidence value can be based on the movement information and the surrounding environment information. For example, when the portable air quality measurement apparatus 230 has moved more than a threshold distance, the portable air quality measurement apparatus 230 may determine that the first air quality related information is invalid (or associate a low confidence value). In another case, the portable air quality measurement apparatus 230 may determine that the first air quality related information is invalid when the ambient illuminance is less than threshold illuminance, or there is an object that is close to a specified distance. The portable air quality measurement apparatus 230 may store the first air quality related information in relation to the determined validity.

When a specified application is executed, the portable air quality measurement apparatus 230 may identify the validity of the first air quality related information, and when the first air quality related information is valid, a first air quality screen configured based on the first air quality related information may be displayed through the specified application. Alternatively, when the first air quality related information is invalid, the portable air quality measurement apparatus 230 may display a second air quality related screen through the specified application based on the second air quality related information received from the server 220. The portable air quality measurement apparatus 230 may display the first or second air quality related screen as, for example, an initial screen of a specified application.

According to the above-described embodiment, the portable air quality measurement apparatus 230 may provide air quality related information that is valid (or reliability) for the user surrounding environment.

Figure 3:
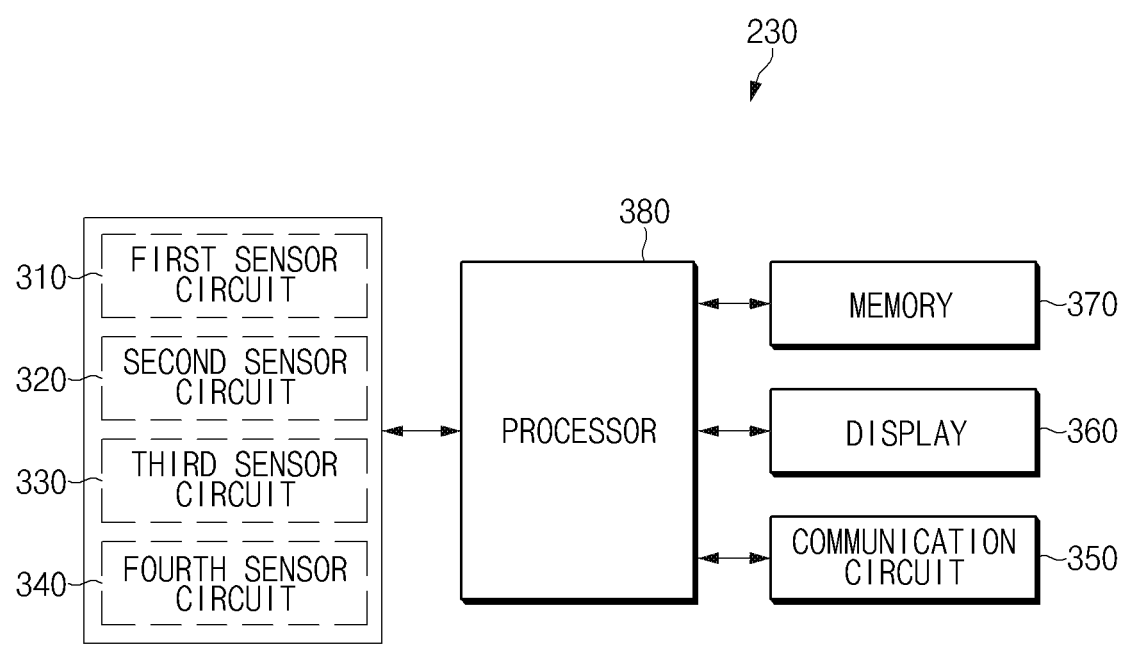
FIG. 3 is a block diagram illustrating a portable air quality measurement apparatus according to an embodiment.

FIG. 3 is a block diagram illustrating a portable air quality measurement apparatus according to an embodiment. The portable air quality measurement apparatus has sensors for determining the air quality information and other sensors for determining the validity of the air quality information. When the determined validity of the air quality information is valid, the air quality information can be used with various other information.

The validity of the air quality information can be determined using other sensors. For example, a sensor can be used to measure movement of the device. If the movement of the device exceeds a threshold, the air quality information can be deemed invalid. In another example, if a very low ambient light is measured and a proximity sensor determines that there is an object within a particular distance, the air quality information can be deemed invalid because the portable air quality measurement apparatus is likely to be inside the user's pocket or a bag.

If the air quality information is deemed invalid, the portable air quality measurement apparatus may request air quality information from a server 220 which provides the air quality information measured by an air quality measurement device 210 proximate to the location of the portable air quality measurement apparatus 230.

Referring to FIG. 3, the portable air quality measurement apparatus (e.g., the portable air quality measurement apparatus 230 of FIG. 2) according to an embodiment may include a first sensor circuit 310 (e.g., the sensor module 176 of FIG. 1), a second sensor circuit 320 (e.g., the sensor module 176 of FIG. 1), a third sensor circuit 330 (e.g., the sensor module 176 of FIG. 1), a fourth sensor circuit 340 (e.g., the sensor module 176 of FIG. 1), a communication circuit 350 (e.g., the communication module 190 of FIG. 1), a display 360 (e.g., the display device 160 of FIG. 1), a memory 370 (e.g., the memory 130 of FIG. 1), and a processor 380 (e.g., the processor 120 of FIG. 1). It shall be understood that "processor" shall refer to both the singular and plurality contexts. In an embodiment, some components may be omitted from the portable air quality measurement apparatus 230, or additional components may be further included. In an embodiment, some of the components of the portable air quality measurement apparatus 230 may be combined to form a single object, and may perform the functions of the corresponding components before being combined.

According to an embodiment, the first sensor circuit 310 may detect the quality of air around the portable air quality measurement apparatus 230. For example, the air quality may include at least one of the quality of fine dust (e.g., PM1, PM2.5, PM10) or the quality of gas ($CO_2$, $NO_2$, $SO_2$, CO, NO, $O_3$, $NH_3$, $H_2S$, total volatile organic compounds (TVOC), volatile organic compounds (VOC), formaldehyde (HCHO), benzene, toluene, ethyl benzene and xylene (BTEX)).

In certain embodiments, the air quality can include information about levels of different pollens, such as tree pollen, grass pollen, ragweed pollen, to name a few.

According to an embodiment, the second sensor circuit 320 may sense the movement of the portable air quality measurement apparatus 230. The second sensor circuit 320 may include at least one of a geomagnetic sensor that senses the direction and sensitivity of the geomagnetic, a gyro sensor that senses an angular velocity of the portable air quality measurement apparatus 230, or an acceleration sensor that senses the acceleration of the portable air quality measurement apparatus 230. In some embodiments, the second sensor may include a satellite positioning system.

According to an embodiment, the third sensor circuit 330 may sense an adjacent environment of the portable air quality measurement apparatus 230. The third sensor circuit 330 may include at least one of an infrared sensor for sensing a near object by transmitting/receiving infrared rays and/or an illuminance sensor for sensing ambient illuminance.

According to an embodiment, the fourth sensor circuit 340 may detect a current location of the portable air quality measurement apparatus 230. The fourth sensor circuit 340 may include a GPS module for detecting a current location based on the GPS signal. The current location may include, for example, latitude, longitude, and altitude.

According to an embodiment, the communication circuit 350 may support the establishment of a wired or wireless communication channel between the portable air quality measurement apparatus 230 and the server 220, and the communication through the established communication channel.

For example, the display 360 may display various contents (e.g., text, images, videos, icons, symbols, and the like). For example, the display 360 may include a liquid crystal display (LCD), a light emitting diode (LED) display, an organic light emitting diode (OLED) display, or an electronic paper display.

For example, the memory 370 may store instructions or data related to at least one of other components of the portable air quality measurement apparatus 230. The memory 370 may be a volatile memory (e.g., RAM, or the like), a nonvolatile memory (e.g., ROM, a flash memory, and the like), or a combination thereof. The memory 370 may store instructions that, when executed, cause the processor 380 to detect the first air quality related information by using the first sensor circuit 310, detect the movement information by using the second sensor circuit 320 and adjacent environment information by using the third sensor circuit 330 while the first air quality related information is detected, determine validity of the first air quality related information based on the adjacent environment information and the movement information, construct a first air quality related screen based on the first air quality related information when it is determined that the first air quality related information is valid, construct a second air quality related screen based on the second air quality related information received from the server 220 when it is determined that the first air quality related information is invalid, and display the first or second air quality related screen through the display 360.

The processor 380 may execute operations or data processing related to control and/or communication of at least one of other components of the portable air quality measurement apparatus 230 by using instructions stored in the memory 370. For example, the processor 380 may include at least one of a central processing unit (CPU), a graphics processing unit (GPU), a microprocessor, an application processor, an application specific integrated circuit (ASIC), and field programmable gate arrays (FPGAs) and may have a plurality of cores.

According to an embodiment, the processor 380 may use the first sensor circuit 310 to detect the first air quality related information. For example, the first air quality related information may include at least one piece of fine dust (e.g., PM1, PM2.5, PM10) information or gas ($CO_2$, $NO_2$, $SO_2$, CO, NO, $O_3$, $NH_3$, $H_2S$, total volatile organic compounds (TVOC), volatile organic compounds (VOC), formaldehyde (HCHO), benzene, toluene, ethyl benzene and xylene (BTEX), and the like) information.

The processor 380 may use the second sensor circuit 320 to detect the movement information, the third sensor circuit 330 to detect the adjacent environment information, while detecting the first air quality related information. For example, the processor 380 may detect the movement information and the adjacent environment information of the portable air quality measurement apparatus 230 in synchronization with the period of detecting the first air quality related information. For example, the movement information may include at least one of the geomagnetic direction, the geomagnetic sensitivity, the angular velocity, or the acceleration. For example, the adjacent environment information may include at least one of ambient illuminance or distance information from a surrounding object.

According to an embodiment, the processor 380 may detect the location information of the portable air quality measurement apparatus 230 by using the fourth sensor circuit 340. The location information may include latitude, longitude and altitude.

The processor 380 may determine whether the portable air quality measurement apparatus 230 is indoors or outdoors based on the location information. Alternatively, the processor 380 may determine whether the portable air quality measurement apparatus 230 is indoors or outdoors based on the movement information and the location information. The processor 380 may store the identified indoor/outdoor related information in relation to the first air quality related information. In the disclosure, storing information or data in the memory 370 may refer to storing information or data in a nonvolatile memory unless otherwise specified.

The processor 380 may track the movement of a user (e.g., the movement of the portable air quality measurement apparatus 230) based on the location information, and detect the first air quality related information based on changes in location and time. Alternatively, when there is a place specified through the setting (by a user) for a specified application, the processor 380 may determine whether the portable air quality measurement apparatus 230 is located at the specified place based on the location information, and may detect the first air quality related information when the portable air quality measurement apparatus 230 is located at the specified place. In addition, the processor 380 may identify the moving speed of the portable air quality measurement apparatus 230 based on the location information, and may differently control the period of detecting the first air quality related information based on the moving speed. Likewise, the processor 380 may differently control the period of detecting the movement information and the adjacent environment information based on the moving speed.

According to an embodiment, the processor 380 may determine the validity of the first air quality related information based on the adjacent environment information and the movement information. For example, when it is identified that the movement of the portable air quality measurement apparatus 230 exceeds a threshold, the processor 380 may determine that the first air quality related information is invalid (e.g., the validity is less than a specified threshold value). The processor 380 may determine that the first air quality related information is invalid when it is identified that a surrounding object is close to the portable air quality measurement apparatus 230 within a specified distance based on the adjacent environment information. When it is identified that the ambient illuminance is less than the threshold illuminance based on the adjacent environment information, the processor 380 may determine that the first air quality related information is invalid. For example, the specified distance or threshold illuminance may be determined experimentally as a criterion for determining whether the portable air quality measurement apparatus 230 is in a pocket or a bag.

While detecting the first air quality related information, the processor 380 may determine the validity of the first air quality related information and, when the first air quality related information is valid, the processor 380 may store the first air quality related information in relation with validity information (information indicating validity) of the first air quality related information.

However, when the first air quality related information is invalid, the processor 380 may not store the first air quality related information in the memory 370. In this case, the processor 380 may not store the movement information, the adjacent environment information, and the location information related to the first air quality related information. According to certain embodiments, while detecting the first air quality related information, the processor 380 may not determine the validity of the first air quality related information, and after storing the first air quality related information in relation with the movement information, the adjacent environment information and the location information, may determine the validity of the first air quality related information when constructing the first air quality related screen (e.g., when a specified application is executed).

According to an embodiment, the processor 380 may identify the movement pattern and the moving speed of the portable air quality measurement apparatus 230 based on the movement information, and may determine whether the portable air quality measurement apparatus 230 is located in a moving unit based on the movement pattern and the moving speed, and a type of moving unit (e.g., a subway, a bus, a passenger car, or the like). When it is determined that the portable air quality measurement apparatus 230 is located in the moving unit, the processor 380 may store the type of the moving unit in relation to the first air quality related information. For example, the processor 380 may compare the movement pattern of the portable air quality measurement apparatus 230 with a reference movement pattern depending on the type of the moving unit, based on the movement information, and compare the moving speed of the portable air quality measurement apparatus 230 with a moving speed depending on the type of the moving unit, thereby identifying the type of the moving unit.

According to an embodiment, when a specified application related to an air quality providing service is executed, the processor 380 may identify (or determine) the validity of the first air quality related information. For example, when the specified application is executed, the processor 380 may identify the validity of the first air quality related information based on whether valid first air quality related information exists in the memory 370 or whether the first air quality related information exists in the memory 370. As another example, the processor 380 may determine the validity of the first air quality related information based on the movement information, the adjacent environment information, and the location information related to the first air quality related information.

According to an embodiment, when the first air quality related information is valid, the processor 380 may construct a first air quality related screen to be displayed through a specified application based on (e.g., using) the first air quality related information. For example, the processor 380 may determine at least one of an air quality related text or an air quality related image based on the first air quality related information, and may construct the first air quality related screen including at least one of the air quality related text or the air quality related image. The air quality related text may include, for example, at least one of a text (e.g., best, very good, good, bad, worst) or a numerical value indicating an air quality index or a fine dust index. The air quality related image may be provided, for example, in a color corresponding to the air quality grade. As another example, the processor 380 may track a change in the location of the portable air quality measurement apparatus 230 based on location information related to the first air quality related information, and may display a map image indicating an air quality grade for each location of the portable air quality measurement apparatus 230 based on the location information and the first air quality related information.

According to an embodiment, the processor 380 may configure a first air quality related screen including at least one of indoor/outdoor information or moving unit type information. For example, when the portable air quality measurement apparatus 230 is located in a building, the processor 380 may construct the first air quality related screen related to the name of the building in which the portable air quality measurement apparatus 230 is located. As another example, when the portable air quality measurement apparatus 230 is located in the moving unit, the processor 380 may configure the first air quality related screen related to the type of the moving unit in which the portable air quality measurement apparatus 230 is located.

According to an embodiment, when the first air quality related information is invalid, the processor 380 may receive the second air quality related information corresponding to the current location from the server 220 and construct the second air quality related screen to be displayed through the application specified based on the second air quality related information. For example, the processor 380 may identify the air quality grade corresponding to the current location and the surrounding locations based on the second air quality related information (e.g., the gas index and the fine dust index) related to the current location and the surrounding locations from the server 220, and configure the second air quality related screen in which the current location and the surrounding locations are indicated in colors corresponding to the identified air quality grades.

According to an embodiment, the processor 380 may display the configured first or second air quality related screen through a specified application (e.g., an initial screen of the specified application).

According to an embodiment, the processor 380 may provide air quality history information of a specified place through a specified application. For example, when the processor 380 receives a request for providing an air quality history of a specified place through an input device (e.g., the input device 150 of FIG. 1), the processor 380 may configure a screen including the first air quality related information related to the first time and the first air quality related information related to a second time detected at the specified place and may display the configured screen through the specified application. In this regard, when the specified place is set through the specified application, the processor 380 may detect the first air quality related information at the specified place.

According to an embodiment, the processor 380 may provide route information that satisfies a specified condition through a specified application. For example, the processor 380 may obtain an input related to a route search function to a destination desired by a user through a specified application. In this case, the processor 380 may determine the route to the destination, in which the air quality satisfies a specified condition, based on at least one of the first or second air quality related information in response to the input. The processor 380 may display the determined route on the map image through the specified application.

According to certain embodiments, the portable air quality measurement apparatus 230 may further include a temperature/humidity sensor circuit capable of sensing at least one of temperature or humidity. In this case, the processor 380 may configure a first air quality related screen including at least one of temperature information and humidity information.

According to certain embodiments, the portable air quality measurement apparatus 230 may be configured of a plurality of electronic devices. For example, the portable air quality measurement apparatus 230 may include a wearable device worn by a user, a mobile phone carried by the user, a portable accessory, an AI speaker, or another IoT device (e.g., indoor dust meter, air cleaner, air conditioner, and the like). One of the wearable device, the mobile phone, the portable accessory, the AI speaker, or another IoT device may detect the first air quality related information, and another one of the wearable device, the mobile phone, the portable accessory, the AI speaker, or another IoT device may display the first or second air quality related screen based on the validity of the first air quality related information. As an example, the wearable device may include the first sensor circuit 310, the second sensor circuit 320, the third sensor circuit 330, the fourth sensor circuit 340, a first processor (e.g., a processor 380), a first memory (e.g., the memory 370), and a first short range communication circuit. The mobile phone, which is a device in which a specified application is installed, may include a second short range communication circuit, a second processor (e.g., the processor 380), and the display 360. In this case, the first processor may detect the first air quality related information by using the plurality of sensor circuits, and determine the validity of the first air quality related information. The first processor may store the first air quality related information in the first memory in relation to the measurement time information, the measurement location information and the validity information. When the specified application is executed in response to a user input, the second processor may request the wearable device to transmit the first air quality related information, and obtain the first air quality related information from the wearable device in response to the request. The second processor may determine whether the first air quality related information is valid based on the validity information of the first air quality related information, and when the first air quality related information is valid, the second processor may configure the first air quality related screen based on the first air quality related information and display the first air quality related screen as the initial screen of a specified application. When the first air quality related information is invalid, the second processor may receive the second air quality related information, configure the second air quality related screen based on the second air quality related information, and display the second air quality related screen as the initial screen of the specified application. According to another embodiment, at least one of the mobile phone, the portable accessory, the AI speaker, or another IoT device may detect the first air quality related information by using the plurality of sensor circuits, and determine the validity of the first air quality related information. The wearable device may receive first air quality related information from at least one of the mobile phone, the portable accessory, the AI speaker, or the another IoT device, and may display the first or second air quality related screen depending on the validity of the first air quality related information. According to certain embodiments, the processor 380 may transmit the first air quality related information to the server 220 through the communication circuit 350. For example, the processor 380 may transmit the valid first air quality related information to the server 220 in relation to at least one of location information, indoor/outdoor information, and moving unit type information. According to certain embodiments, the processor 380 may transmit the detected first air quality related information to the server 220 in relation to the validity information (e.g., information about validity).

According to the above-described embodiment, the portable air quality measurement apparatus 230 may be a device that is carried by the user or located close to the user. Accordingly, the portable air quality measurement apparatus 230 may detect air quality related information around the user, and provide the air quality related information valid therein to the user.

In addition, according to the above-described embodiment, when the portable air quality measurement apparatus 230 is in an environment such as a bag or pocket in which it is difficult to measure the outside air quality, or moves severely and sufficiently to change the flow of surrounding gas, the processor 380 may determine the first air quality related information is invalid, and prevent the air quality related information (or information) from being incorrectly provided to the user due to the invalid first air quality related information.

In addition, according to the above-described embodiment, the portable air quality measurement apparatus 230 may share the detected first air quality related information with the server 220, such that another electronic device provides information about air quality around the user of another electronic device through the server 220.

The first air quality related information can be stored with the measurement time, location, an indoor or outdoor indicator, and validity information in memory.

FIG. 4 is a table illustrating first air quality related information stored in a memory (e.g., the memory 370 of FIG. 3) according to an embodiment. The first air quality related information is stored as chart that includes measurement time 371 and location 372. For each measurement time 371, the location 372, first air quality related information 373, indoor/outdoor information 374, and validity information 375 is stored.

Referring to FIG. 4, first air quality related information 373 according to an embodiment may be stored in the memory 370, for example, in the form of a lookup table in relation to detection time information 371, detection location information 372, and validity information 375. The first air quality related information may include, for example, at least one of fine dust (e.g., PM1, PM2.5, and PM10) information or gas ($CO_2$, $NO_2$, $SO_2$, CO, NO, $O_3$, $NH_3$, $H_2S$, total volatile organic compounds (TVOC), volatile organic compounds (VOC), formaldehyde (HCHO), benzene, toluene, ethyl benzene and xylene (BTEX), and the like) information. In certain embodiments, the first air quality information may include information about different pollen counts. The detection time information 371 may include, for example, information about a date and time at which the first air quality related information 373 is detected. For example, the detection location information 372 may include the latitude and longitude of a location where the first air quality related information 373 is detected. The detection location information 372 may further include, for example, an altitude of the location where the first air quality related information 373 is detected. For example, the validity information 375 may include at least one of a numerical value (e.g., 9.8) corresponding to the validity or a sign indicating the validity (e.g., O, X).

According to certain embodiments, the first air quality related information 373 may be stored in relation to indoor/outdoor information 374 or moving unit type information (not shown). For example, the indoor/outdoor information 374 may be displayed as 'Indoor'/'Outdoor' or as a specific location (e.g., a house, company or school corresponding to an indoor place, or a park, playground or mountain corresponding to an outdoor place).

According to an embodiment, the portable air quality measurement apparatus 230 of FIG. 3 may identify (or determine) the validity of the first air quality related information 373 by using the validity information 375. For example, the portable air quality measurement apparatus 230 may obtain the numerical value of the validity information 375 by using at least one of the second sensor circuit 320, the third sensor circuit 330, or the fourth sensor circuit 340.

For example, the portable air quality measurement apparatus 230 may quantify the relationship between the degree of movement of the portable air quality measuring apparatus 230 and the validity (e.g., the validity information 375 is displayed as a numerical value (e.g., 0 to 10) of a specific section in inverse proportion to the acceleration of the portable air quality measurement apparatus 230) based on the movement information measured through the second sensor circuit 320 (e.g., a geomagnetic sensor, a gyro sensor, or an acceleration sensor). The portable air quality measurement apparatus 230 may quantify the relationship between the surrounding environment state of the portable air quality measuring apparatus 230 and the validity (e.g., the validity information 375 is displayed as a numerical value (e.g., 0 to 10) of a specific section in proportion to the proximity distance or surrounding illuminance of the portable air quality measurement apparatus 230) based on the surrounding environment information measured through the third sensor circuit 330 (e.g., a proximity sensor or an illuminance sensor). The portable air quality measurement apparatus 230 may quantify the relationship between the moving speed of the portable air quality measurement apparatus 230 and the validity (e.g., the validity information 375 is displayed as a numerical value (e.g., 0 to 10) of a specific section in inverse proportion to the moving speed of the portable air quality measurement apparatus 230) based on the current location information measured through the fourth sensor circuit 340 (e.g., a GPS module).

In certain embodiments, the portable air quality measuring apparatus 230 may quantify the relationship between degree of movement, surrounding environment state, moving speed, and location, and determine a weighted average of the foregoing to determine the numerical value of the validity.

The portable air quality measurement apparatus 230 may compare the quantified validity information 375 with a threshold value to determine (or identify) whether the first air quality related information 373 is valid.

Figure 5:
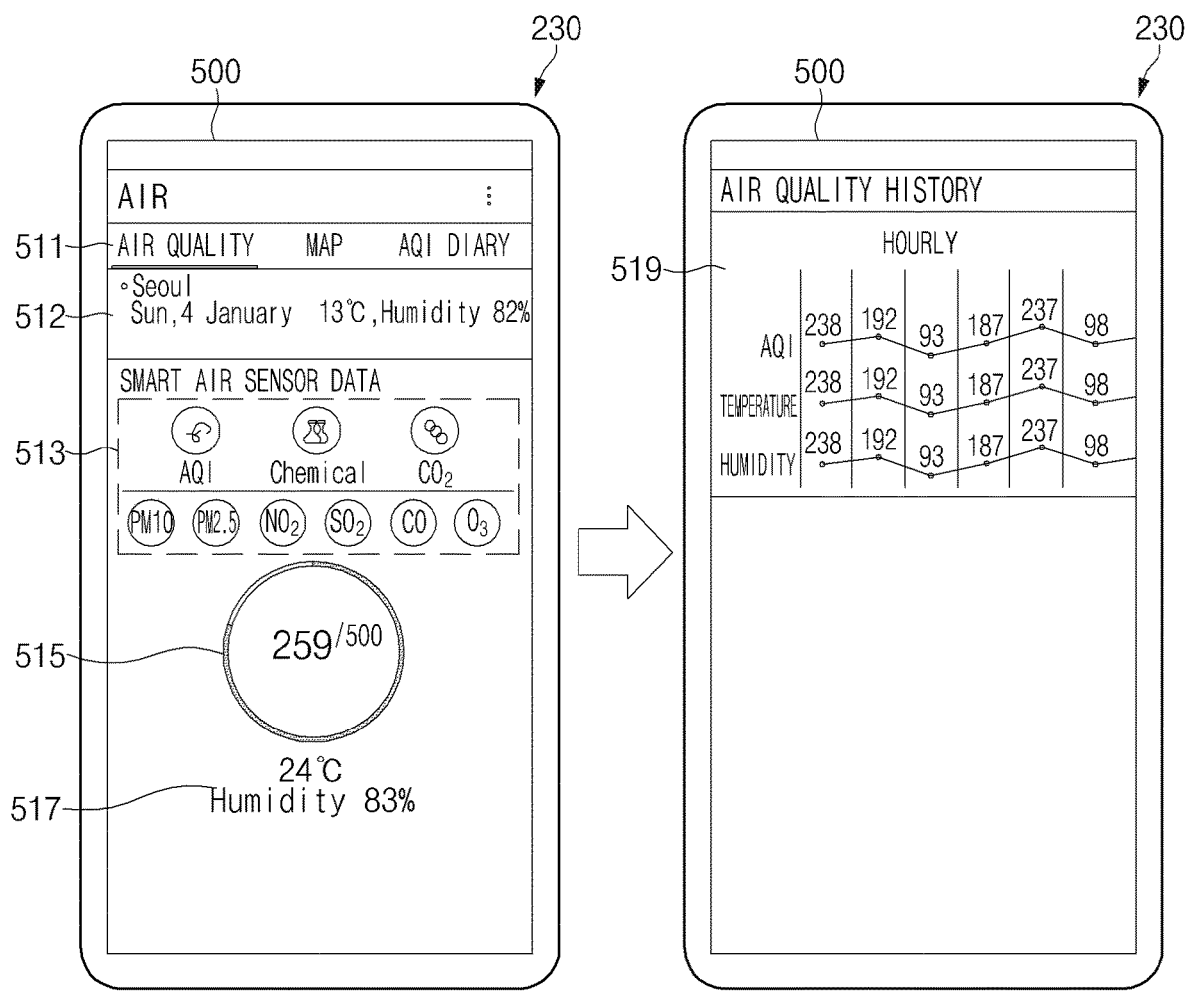
FIG. 5 is a view illustrating an air quality related index screen according to an embodiment.

FIG. 5 is a view illustrating an air quality related index screen according to an embodiment.

Referring to FIG. 5, a portable air quality measurement apparatus (e.g., the portable air quality measurement apparatus 230 of FIG. 2) may display an air quality related index screen 500 (e.g., a first air quality related screen) including weather forecast information 512, air quality item information 513, and air quality index information 515 corresponding to a selected item based on the first air quality related information.

For example, the portable air quality measurement apparatus 230 may determine that the first air quality related information is valid when an air quality index providing menu 511 (AIR QUALITY) is selected by the user (or when a specified application is executed). In this case, the portable air quality measurement apparatus 230 may receive the weather forecast information 512 corresponding to the current location from the server 220, identify the air quality index corresponding to the selected air quality item (e.g., $NO_2$) based on the first air quality related information. The portable air quality measurement apparatus may then display the air quality related index screen 500 including the weather forecast information 512, the air quality item information 513 capable of distinguishing selected/unselected air quality items, and the air quality index information 515 corresponding to the selected air quality items. The air quality item information 513 may include button objects related to the type of fine dust (e.g., PM2.5, PM10) or a gas name (e.g., $NO_2$, $SO_2$, CO, NO, $O_3$, $CO_2$) (and in certain embodiments, different pollen levels) sensed by the portable air quality measurement apparatus 230. In addition, the air quality item information 513 may include button objects related to the chemical index item sensed by the portable air quality measurement apparatus 230. The air quality index information 515 may include an air quality index (e.g., $NO_2$) corresponding to the selected air quality item information. According to certain embodiments, the air quality related index screen 500 may include air quality index history information 519 (e.g., today hourly air quality index information, weekly air quality index information, or monthly air quality index information) corresponding to the selected item. The portable air quality measurement apparatus 230 may provide the weather forecast information 512, the air quality item information 513, the air quality index information 515, and the air quality index history information 519 to a plurality of pages.

Figure 6:
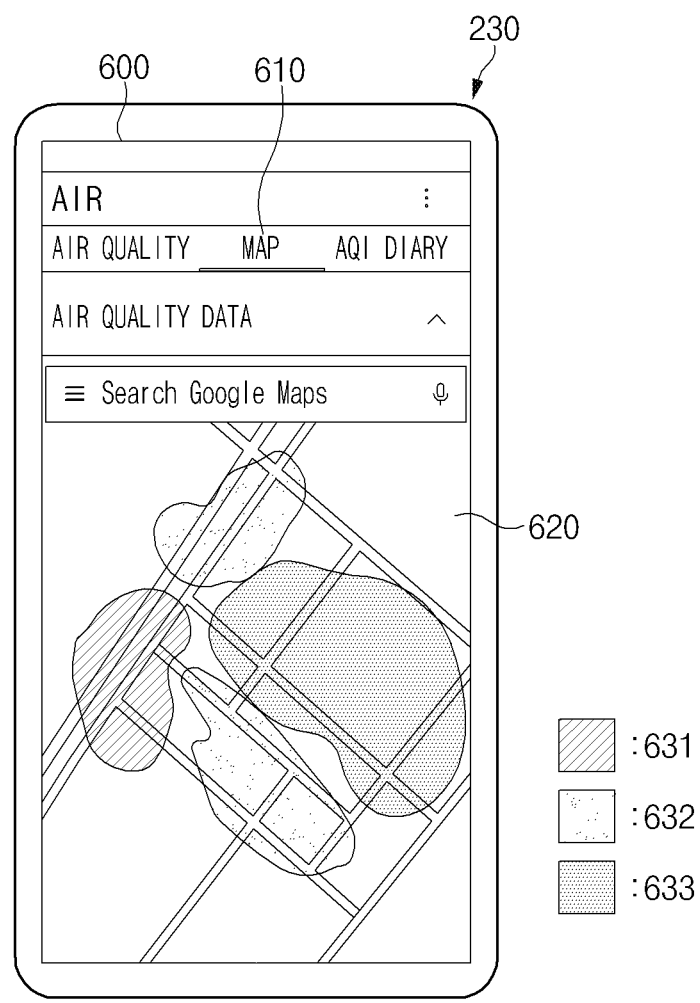
FIG. 6 is a view illustrating an example of an air quality related map screen according to an embodiment.

FIG. 6 is a view illustrating an example of an air quality related map screen according to an embodiment.

Referring to FIG. 6, a portable air quality measurement apparatus (e.g., the portable air quality measurement apparatus 230 of FIG. 2) may provide an air quality related map screen 600 (e.g., the second air quality related screen) in which objects 631 to 633 of colors corresponding to the air quality grades of each area included in a map image are displayed while being overlapped. For example, the portable air quality measurement apparatus 230 may identity that the first air quality related information is invalid when an air quality map providing menu 610 (MAP) is selected by the user (or when a specified application is executed). In this case, the portable air quality measurement apparatus 230 may receive second air quality related information within a specified range from a current location from a server (e.g., the server 220 of FIG. 2). The portable air quality measurement apparatus 230 may display the objects 631 to 633 of colors corresponding to the air quality grades of each area included in a map image to be overlapped on the map image including a current location based on the second air quality related information. The colors 631 to 633 corresponding to the air quality grades may be set differently according to the air quality grades (e.g., best ⇔ green, good ⇔ yellow, bad ⇔ red, and worst ⇔ purple).

In certain embodiments, the air quality grades can be based on a numerical value that is derived based on a weighted average of the different chemical levels, and further include pollen counts. Ranges of the weighted averages can be associated with the different colors. The color associated with the weighted average for the air at a particular location can then be displayed.

Figure 7:
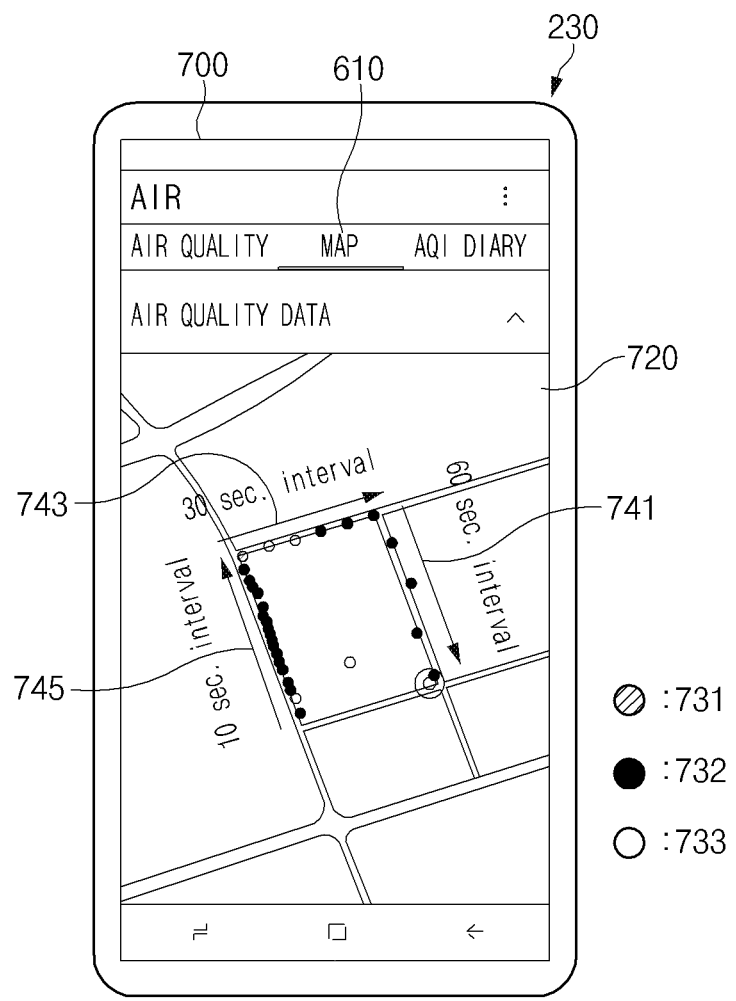
FIG. 7 is a view illustrating another example of an air quality related map screen according to an embodiment.

FIG. 7 is a view illustrating another example of an air quality related map screen according to an embodiment. The user locations can be tracked with a colored marker indicating the air quality at the location.

Referring to FIG. 7, a portable air quality measurement apparatus (e.g., the portable air quality measurement apparatus 230 of FIG. 2) may track a location change (or a change in the location of a user) of the portable air quality measurement apparatus 230, and provide an air quality related map screen 700 (e.g., the first air quality related screen) displaying an object (e.g., a circle) of a color corresponding to an air quality grade according to the location change in a map image. For example, the portable air quality measurement apparatus 230 may identify that the first air quality related information is valid when the air quality map providing menu 610 (MAP) is selected by the user (or when a specified application is executed). In this case, the portable air quality measurement apparatus 230 may identify the air quality grade according to the location change of the portable air quality measurement apparatus 230 based on the first air quality related information, and display objects 731 to 733 of color corresponding to the identified air quality grade in a map image 720.

In this regard, the portable air quality measurement apparatus 230 may periodically detect the first air quality related information corresponding to the location change. The portable air quality measurement apparatus 230 may identify the moving speed of the portable air quality measurement apparatus 230 based on the location information, and detect the first air quality related information corresponding to the moving speed at different sampling rates. For example, when the moving speed is 4 to 7 km/h (e.g., a walking speed of the user), the first air quality related information may be detected at intervals of 60 seconds (section 741). When the moving speed is 10 to 15 km/h (e.g. a running speed of the user), the first air quality related information may be detected at intervals of 30 seconds (section 743). When the moving speed is 15 to 20 km/h (e.g. a bicycle speed), the first air quality related information may be detected at intervals of 10 seconds (section 745).

According to certain embodiments, the information 631, 632, 633, 731, 732, and 733 of FIGS. 6 and 7 may be displayed together.

Figure 8:
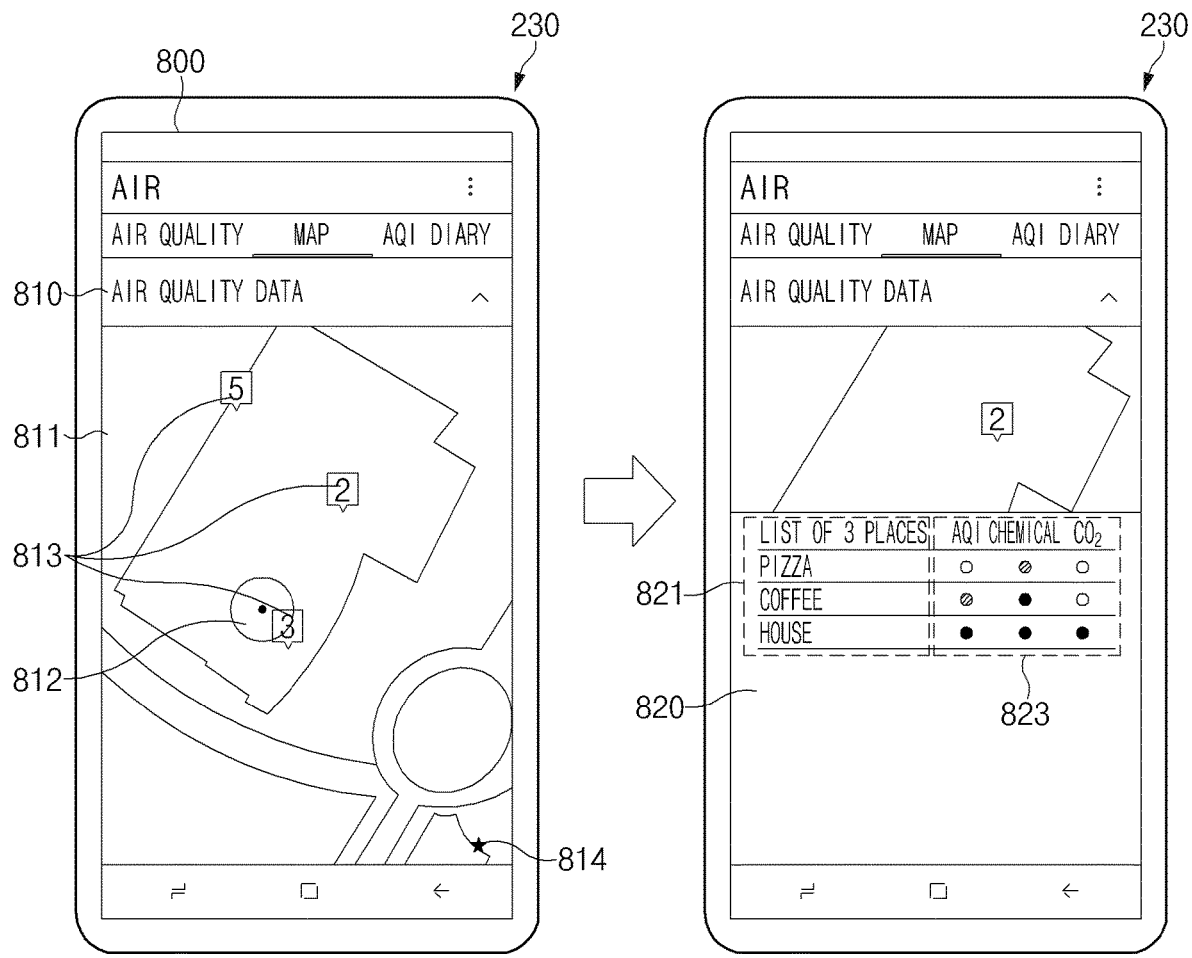
FIG. 8 illustrates another example of an air quality related map screen according to an embodiment.

FIG. 8 illustrates another example of an air quality related map screen according to an embodiment.

Referring to FIG. 8, a portable air quality measurement apparatus (e.g., the portable air quality measurement apparatus 230 of FIG. 2) according to an embodiment may configure an air quality related map screen 810 based on first or second air quality related information, and provide the configured air quality related map screen 810 through a specified application. For example, the air quality related map screen 810 may include objects 812, 813, and 814. Object 812 indicates a current location of the portable air quality measurement apparatus 230. Object 813 indicates a location of an ambient air quality measurement apparatus. Button object 814 can be for requesting to display second air quality related information. When the button object 814 is selected by the user, the portable air quality measurement apparatus 230 may receive ambient air quality measurement apparatus information 821 and second air quality related information 823 through the server 220, and display the ambient air quality measurement apparatus information 821 and the second air quality related information 823. The ambient air quality measurement apparatus information 821 may include a name of the ambient air quality measurement apparatus or a place name of the ambient air quality measurement apparatus. The second air quality related information 823 may be detected (or provided) from the ambient air quality measurement apparatus.

Figure 9:
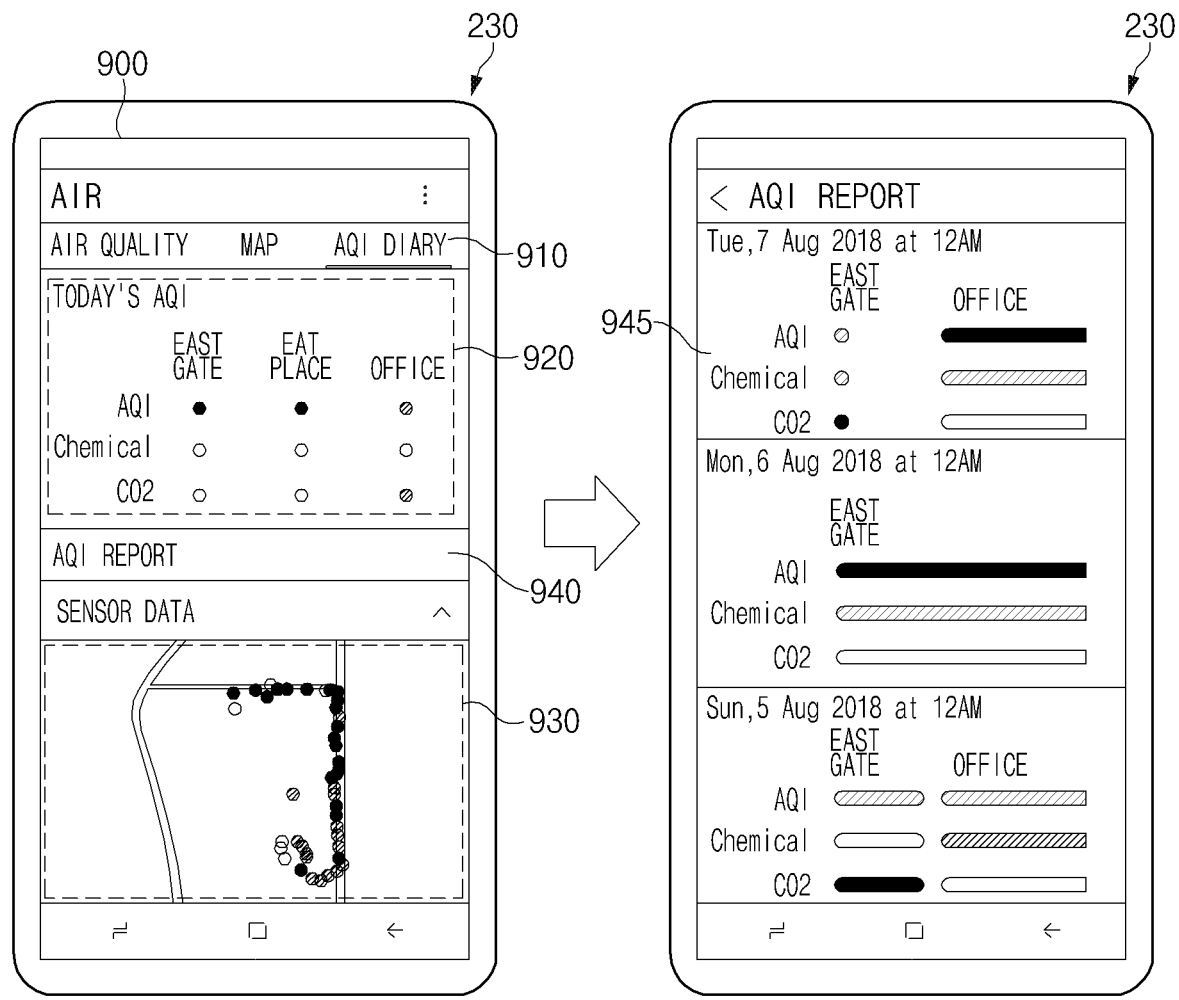
FIG. 9 a view illustrating an air quality related history screen according to an embodiment.

FIG. 9 a view illustrating an air quality related history screen according to an embodiment.

Referring to FIG. 9, a portable air quality measurement apparatus (e.g., the portable air quality measurement apparatus 230 of FIG. 2) according to an embodiment may provide an air quality related history screen 900 (e.g., the first air quality related screen) corresponding to a plurality of places based on the first air quality related information detected at the plurality of places (specified places). For example, the plurality of places may include a first place (EAST GATE), a second place (EAT PLACE), and a third place (OFFICE). For example, the portable air quality measurement apparatus 230 may provide the air quality related history screen 900 including air quality index information 920 and air quality tracking information 930 for each place based on the first air quality related information detected at the plurality of places when an air quality history providing menu 910 (AQI DIARY) is selected by a user (or when a specified application is executed). The air quality index information 920 for each place may include, for example, air quality index information (e.g., including an air quality index for each air quality item) corresponding to each of the plurality of places. For example, the air quality tracking information 930 may include a map image and an air quality grade related object (e.g., an object of a color corresponding to the air quality grade for each location) corresponding to a time change and a location change of the portable air quality measurement apparatus 230 displayed on the map image. The air quality related history screen 900 may further include a button object 940 related to displaying of air quality history information. When the button object 940 is selected, the portable air quality measurement apparatus 230 may display air quality history information 945 corresponding to time changes corresponding to the plurality of places.

Figure 10:
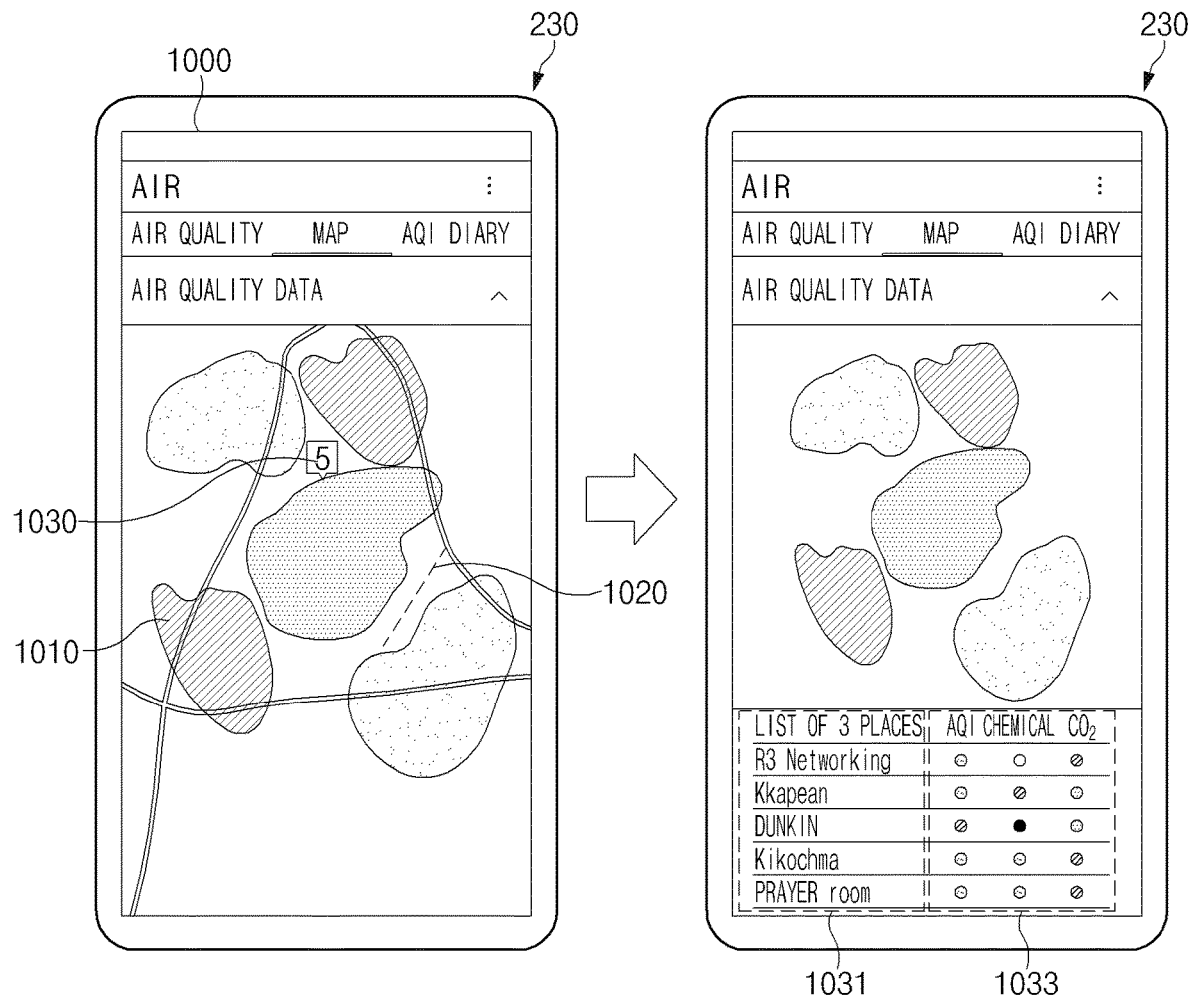
FIG. 10 is a view illustrating still another example of an air quality related map screen according to an embodiment.

FIG. 10 is a view illustrating still another example of an air quality related map screen according to an embodiment.

Referring to FIG. 10, a portable air quality measurement apparatus (e.g., the portable air quality measurement apparatus 230 of FIG. 2) may provide an air quality related map screen 1000 including a first object 1010 indicating an outside air quality, and a second object 1020 indicating air quality corresponding to a location change, and a third object 1030 indicating the air quality of each place. For example, the first object 1010 may be a cloud-shaped object of a color corresponding to an air quality grade covering an area having the same air quality grade. The second object 1020 may be a dot or line-shaped object indicating the air quality grade corresponding to the location change of the portable air quality measurement apparatus 230. The third object 1030 may include a number indicating the number of air quality related information detected at each place.

The portable air quality measurement apparatus 230 may provide air quality index information 1031 and 1033 corresponding to the first air quality related information detected at each place. For example, when the third object 1030 is selected, the portable air quality measurement apparatus 230 may provide each place information 1031 (e.g., place name information) and air quality index information 1033 for each place. For example, the air quality index information 1033 for each place may include an air quality grade object (e.g., a circle having a color corresponding to a grade) for each air quality item detected at the places.

Figure 11:
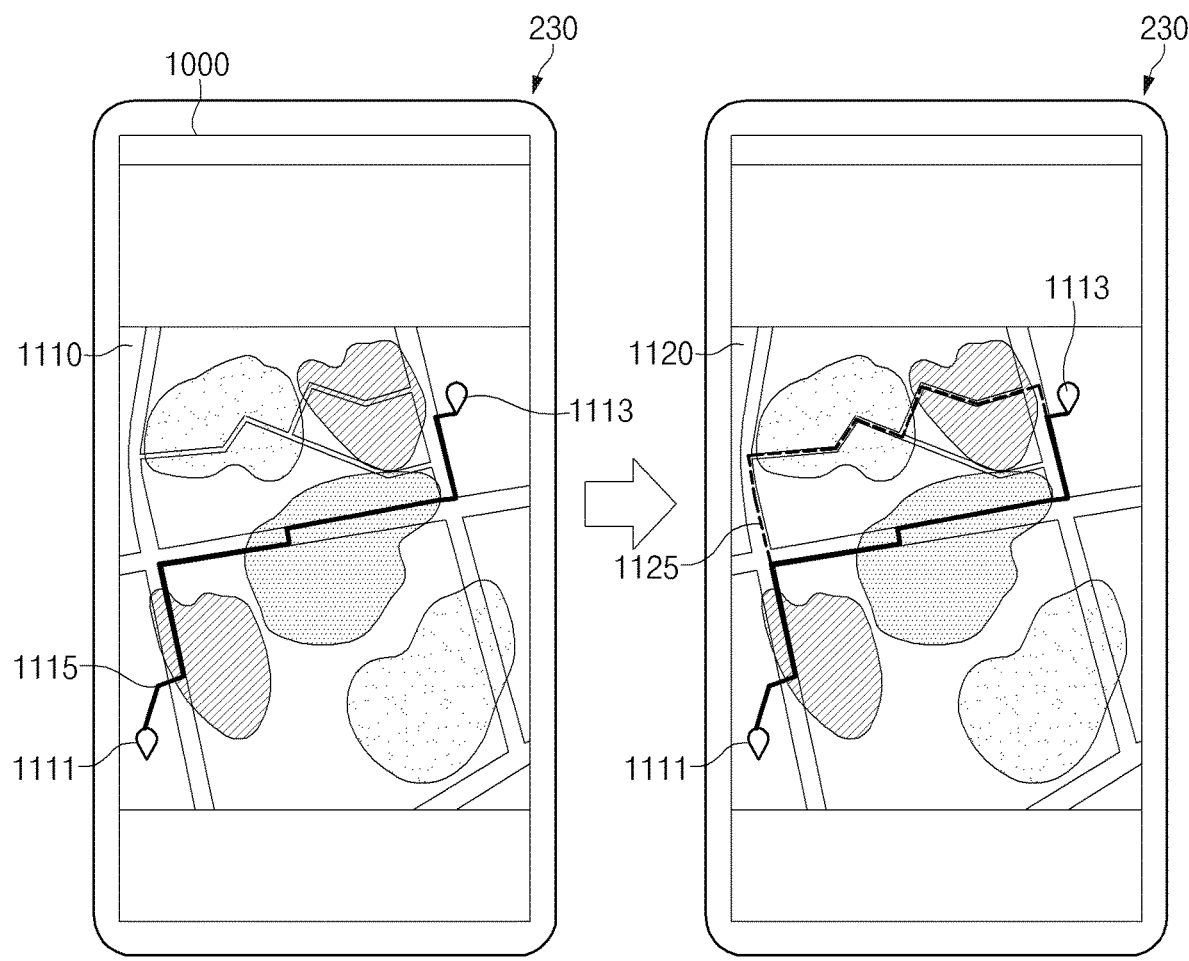
FIG. 11 is a view illustrating an air quality related route guide screen according to an embodiment.

FIG. 11 is a view illustrating an air quality related route guide screen according to an embodiment.

Referring to FIG. 11, a portable air quality measurement apparatus (e.g., the portable air quality measurement apparatus 230 of FIG. 2) may guide a route to a destination in which the air quality meets a specified condition based on at least one of the first or second air quality related information. The specified condition may be having an air quality having air quality information exceeding a predetermined threshold.

According to an embodiment, the portable air quality measurement apparatus 230 may identify an input related to a route search to a destination, perform a route search from a departure 1111 to a destination 1113 in response to the input, and display a searched route 1115 in the map image on a screen 1110 (an air quality related route guidance screen). When the portable air quality measurement apparatus 230 identifies that the searched route includes an area (e.g., an area whose air quality is lower than a threshold grade) in which the air quality does not satisfy the specified condition, the portable air quality measurement apparatus 230 may re-search for a route including only an area that satisfies a specified condition, and display a re-searched route 1125 on a screen 1120.

Figure 12:
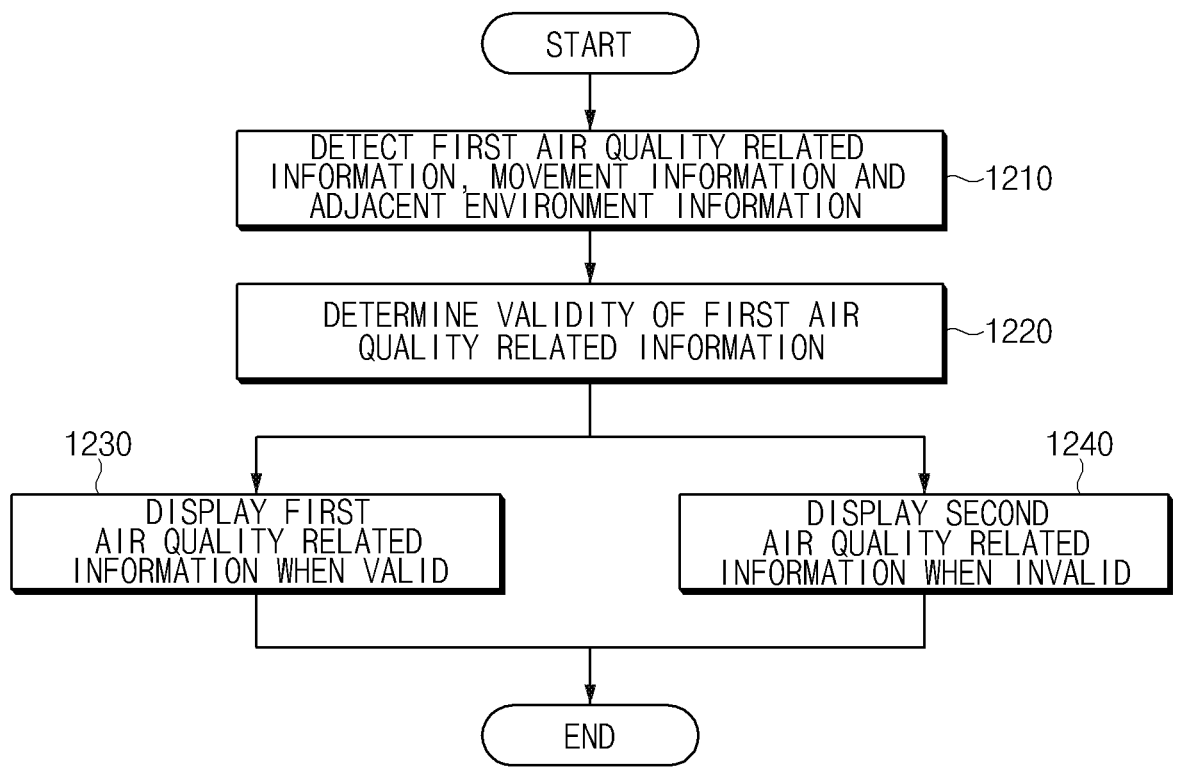
FIG. 12 is a flowchart illustrating a method of displaying air quality related information according to an embodiment.

FIG. 12 is a flowchart illustrating a method of displaying air quality related information according to an embodiment.

Referring to FIG. 12, in operation 1210, a portable air quality measurement apparatus (e.g., the portable air quality measurement apparatus 230 of FIG. 2) may detect the first air quality related information by using the first sensor circuit 310. While detecting the first air quality related information, the portable air quality measurement apparatus 230 may detect movement information by using the second sensor circuit 320 and detect adjacent environment information by using the third sensor circuit 330. For example, the first air quality related information may include at least one of fine dust information or gas information. For example, the movement information may include at least one of the geomagnetic direction, the geomagnetic sensitivity, the angular velocity, or the acceleration. For example, the adjacent environment information may include at least one of surrounding illuminance and information about a distance from a surrounding object.

In operation 1220, the portable air quality measurement apparatus 230 may determine the validity of the first air quality related information based on the adjacent environment information and the movement information. For example, the portable air quality measurement apparatus 230 may determine that the first air quality related information is invalid when it is identified that the movement of the portable air quality measurement apparatus 230 is greater than or equal to a specified size based on the movement information, it is identified that the distance between a surrounding object and the portable air quality measurement apparatus 230 is less than a specified distance based on the adjacent environment information, or it is identified that the ambient illuminance is less than threshold illuminance based on the adjacent environment information.

In operation 1230, the portable air quality measurement apparatus 230 may display the first air quality related information when the first air quality related information is valid (e.g., when the determined validity is greater than or equal to a threshold value). For example, the processor 380 may determine at least one of an air quality related text or an air quality related image based on the first air quality related information, and may display the first air quality related screen including at least one of the air quality related text or air quality related image. For example, the air quality related text may include at least one of a text or a numerical value indicating a gas index (an air quality index) or a fine dust index (e.g., best, very good, good, bad, worst). For example, the air quality related image may be provided in a color corresponding to the air quality grade. In another example, the processor 380 may track a location change of the portable air quality measurement apparatus 230 based on the location information related to the first air quality related information, and display a map image indicating an air quality grade for each location of the portable air quality measurement apparatus 230 based on the location information and the first air quality related information.

In operation 1240, the portable air quality measurement apparatus 230 may display the second air quality related information received from the external server when the first air quality related data is invalid (e.g., when the determined validity is less than a threshold value). For example, the portable air quality measurement apparatus 230 may display objects of a color corresponding to the air quality grade of the area included in the map image to overlap with the map image.

The electronic device according to certain embodiments may be one of various types of electronic devices. The electronic devices may include, for example, a portable communication device (e.g., a smartphone), a computer device, a portable multimedia device, a portable medical device, a camera, a wearable device, or a home appliance. According to an embodiment of the disclosure, the electronic devices are not limited to those described above.

It should be appreciated that certain embodiments of the disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B", "at least one of A and B", "at least one of A or B", "A, B, or C", "at least one of A, B, and C", and "at least one of A, B, or C" may include any one of, or all possible combinations of the items enumerated together in a corresponding one of the phrases. As used herein, such terms as "1st" and "2nd", or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with", "coupled to", "connected with", or "connected to" another element (e.g., a second element), it means that the element may be coupled with the other element directly (e.g., wiredly), wirelessly, or via a third element.

As used herein, the term "module" may include a unit implemented in hardware, software, or firmware, and may interchangeably be used with other terms, for example, "logic", "logic block", "part", or "circuitry". A module may be a single integral component, or a minimum unit or part thereof, adapted to perform one or more functions. For example, according to an embodiment, the module may be implemented in a form of an application-specific integrated circuit (ASIC).

Certain embodiments as set forth herein may be implemented as software (e.g., the program 140) including one or more instructions that are stored in a storage medium (e.g., internal memory 136 or external memory 138) that is readable by a machine (e.g., the electronic device 101). For example, a processor (e.g., the processor 120) of the machine (e.g., the electronic device 101) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a compiler or a code executable by an interpreter. The machine-readable storage medium may be provided in the form of a non-transitory storage medium. Wherein, the term "non-transitory storage medium" means a tangible device, and does not include a signal (e.g., an electromagnetic wave), but this term does not differentiate between where data is semi-permanently stored in the storage medium and where the data is temporarily stored in the storage medium. For example, "the non-transitory storage medium" may include a buffer where data is temporally stored.

According to an embodiment, a method according to certain embodiments of the disclosure may be included and provided in a computer program product. The computer program product may be traded as a product between a seller and a buyer. The computer program product (e.g., downloadable app)) may be distributed in the form of a machine-readable storage medium (e.g., compact disc read only memory (CD-ROM)), or be distributed (e.g., downloaded or uploaded) online via an application store (e.g., PlayStore™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to certain embodiments, each component (e.g., a module or a program) of the above-described components may include a single entity or multiple entities. According to certain embodiments, one or more of the above-described components may be omitted, or one or more other components may be added. Alternatively or additionally, a plurality of components (e.g., modules or programs) may be integrated into a single component. In such a case, according to certain embodiments, the integrated component may still perform one or more functions of each of the plurality of components in the same or similar manner as they are performed by a corresponding one of the plurality of components before the integration. According to certain embodiments, operations performed by the module, the program, or another component may be carried out sequentially, in parallel, repeatedly, or heuristically, or one or more of the operations may be executed in a different order or omitted, or one or more other operations may be added.

According to the embodiments, it is possible to provide information about air quality around a user. In addition, various effects that are directly or indirectly understood through the present disclosure may be provided.

While the disclosure has been shown and described with reference to certain embodiments thereof, it will be understood by those skilled in the art that various changes in form and details may be made therein without departing from the spirit and scope of the disclosure as defined by the appended claims and their equivalents.

What is claimed is:

1. An apparatus for measuring air quality, the apparatus comprising:
  a first sensor circuit configured to sense an external air quality;
  a second sensor circuit configured to sense a movement of the apparatus;
  a third sensor circuit configured to sense an environment of the apparatus;
  a communication circuit configured to communicate with an external server;
  a display;
  a processor; and
  a memory,
  wherein the memory stores instructions that, when executed, cause the processor to:
  detect air quality related information by using the first sensor circuit,
  obtain at least one of movement information detected by using the second sensor circuit or adjacent environment information detected by using the third sensor circuit while the air quality related information is detected by the first sensor circuit,
  determine validity of the air quality related information from using the first sensor circuit based on at least one of the adjacent environment information or the movement information,
  display the air quality related information from using the first sensor circuit through the display when the determined validity is equal to or greater than a threshold value, and display air quality related information received from the external server through the display when the determined validity is less than the threshold value.

2. The apparatus of claim 1, wherein the instructions, when executed, cause the processor to:
identify the validity of the air quality related information from the first sensor circuit when a specified application is executed, and
receive the air quality related information from the external server when the identified validity is less than the threshold value.

3. The apparatus of claim 1, wherein the instructions, when executed, cause the processor to:
determine the validity of the air quality related information from the first sensor circuit while the air quality related information is detected by the first sensor circuit,
store the air quality related information from the first sensor circuit when the determined validity is equal to or greater than the threshold value, and
discard the air quality related information from the first sensor circuit when the determined validity is less than the threshold value.

4. The apparatus of claim 1, wherein the instructions, when executed, cause the processor to:
determine that the validity of the air quality related information from the first sensor circuit is less than the threshold value when the movement of the apparatus that is greater than or equal to a specified size is identified based on the movement information, a distance between a surrounding object and the apparatus that is less than a specified distance is identified based on the adjacent environment information, or ambient illuminance of the apparatus that is less than specified illuminance is identified based on the adjacent environment information.

5. The apparatus of claim 1, further comprising:
a fourth sensor circuit configured to identify a current location of the apparatus,
wherein the instructions, when executed, cause the processor to:
detect current location information by using the fourth sensor circuit while the air quality related information is detected by the first sensor circuit, and
display the air quality related information from the first sensor circuit in relation to the current location identified from the current location information.

6. The apparatus of claim 5, wherein the instructions, when executed, cause the processor to:
determine whether the apparatus is indoors or outdoors based on the current location information, and
display the air quality related information from the first sensor circuit in relation to indoors or outdoors.

7. The apparatus of claim 5, wherein the instructions, when executed, cause the processor to:
identify a movement pattern and a moving speed of the apparatus based on the movement information,
identify whether the apparatus is located in a moving unit and a type of the moving unit based on the movement pattern and the moving speed, and
display the air quality related information from the first sensor circuit in relation to the identified moving unit when the apparatus is located in the moving unit.

8. The apparatus of claim 5, wherein the instructions, when executed, cause the processor to:
identify a moving speed of the apparatus based on the current location information, and
differently control a period of detecting the air quality related information from the first sensor circuit based on the moving speed.

9. The apparatus of claim 5, wherein the instructions, when executed, cause the processor to:
determine whether the apparatus is located in a specified place based on the current location information,
obtain the air quality related information from the first sensor circuit and identify a first time for which the apparatus is located in the specified place when the apparatus is located in the specified place, and
store the specified place, the first time and the air quality related information from the first sensor circuit.

10. The apparatus of claim 9, wherein the instructions, when executed, cause the processor to:
provide the air quality related information from the first sensor circuit related to the first time obtained at the specified place and the air quality related information from the first sensor circuit related to a second time different from the first time obtained at the specified place.

11. The apparatus of claim 1, wherein the instructions, when executed, cause the processor to:
transmit the air quality related information from the first sensor circuit to the external server through the communication circuit.

12. The apparatus of claim 1, wherein the instructions, when executed, cause the processor to:
identify an input related to searching for a route to a destination,
determine the route to the destination that satisfies a specified condition of air quality based on at least one of the air quality related information from the first sensor circuit or the air quality related information received from the server in response to the input, and
display the determined route on a map image.

13. A method of displaying air quality related information through an air quality measurement apparatus, the method comprising:
detecting air quality related information by using a first sensor circuit;
obtaining at least one of movement information detected by using a second sensor circuit or adjacent environment information detected by using a third sensor circuit while the air quality related information is detected by the first sensor circuit;
determining validity of the air quality related information from the first sensor circuit based on at least one of the adjacent environment information or the movement information;
displaying the air quality related information from the first sensor circuit through the display when the determined validity is equal to or greater than a threshold value; and
displaying air quality related information received from an external server when the determined validity is less than the threshold value.

14. The method of claim 13, wherein the determining the validity of the air quality related information includes:
determining the validity of the air quality related information from the first sensor circuit; and
storing the air quality related information from the first sensor circuit when the determined validity is equal to or greater than the threshold value, and discarding the air quality related information from the first sensor circuit when the determined validity is less than the threshold value.

15. The method of claim 14, wherein the determining of the validity includes:
determining that the validity of the air quality related information from the first sensor circuit is less than the threshold value when a movement of the air quality measurement apparatus that is greater than or equal to a specified size is identified based on the movement information, a distance between a surrounding object and the air quality measurement apparatus that is less than a specified distance is identified based on the adjacent environment information, or ambient illuminance of the air quality measurement apparatus that is less than specified illuminance is identified based on the adjacent environment information.

16. The method of claim 13, wherein the displaying of the air quality related information from the first sensor circuit includes:
determining whether the air quality measurement apparatus is indoors or outdoors based on current location information detected by using a fourth sensor circuit while the air quality related information from the first sensor circuit is detected, and
displaying the air quality related information from the first sensor circuit in relation to indoors or outdoors.

17. The method of claim 13, wherein the detecting of the movement information includes:
identifying a movement pattern and a moving speed of the air quality measurement apparatus based on the movement information; and
identifying whether the air quality measurement apparatus is located in a moving unit and a type of the moving unit based on the movement pattern and the moving speed, and
wherein the displaying of the air quality related information from the first sensor circuit includes:
displaying the air quality related information from the first sensor circuit in relation to the identified moving unit when the air quality measurement apparatus is located in the moving unit.

18. The method of claim 13, wherein detecting includes:
identifying a moving speed of the air quality measurement apparatus based on current location information detected by using a fourth sensor circuit while the air quality related information from the first sensor circuit is detected; and
differently controlling a period of detecting the air quality related information from the first sensor circuit based on the moving speed.

19. The method of claim 13, wherein detecting includes:
identifying whether the air quality measurement apparatus is located in a specified place based on current location information of the air quality measurement apparatus;
obtaining the air quality related information from the first sensor circuit and identifying a first time for which the air quality measurement apparatus is located in the specified place when the air quality measurement apparatus is located in the specified place; and
storing the specified place, the first time and the air quality related information from the first sensor circuit.

20. The method of claim 19, wherein the displaying of the air quality related information from the first sensor circuit includes:
displaying the air quality related information from the first sensor circuit related to the first time obtained at the specified place and the air quality related information from the first sensor circuit related to a second time different from the first time at the specified place.

* * * * *